US00PP33339P2

(12) United States Plant Patent
van Langen

(10) Patent No.: US PP33,339 P2
(45) Date of Patent: Aug. 10, 2021

(54) ***ALOE* PLANT NAME 'AMIAL1823'**

(50) Latin Name: *Gonialoe variegata*
Varietal Denomination: AMIAL1823

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 16/350,414

(22) Filed: Nov. 13, 2018

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373

CPC ... A01H 5/12; A01H 5/02; A01H 5/00; A01H 5/0255; A01H 6/00
See application file for complete search history.

(56) References Cited

PUBLICATIONS

Manning et al. A Molecular Phylogeny and Generic Classification of Asphodelaceae Subfamily Alooideae: A Final Resolution of the Prickly Issue of Polyphyly and the Alooids?, Systematic Botany, (2014) 39(1): 55-74 (Year: 2014).*

* cited by examiner

*Primary Examiner* — June Hwu
(74) *Attorney, Agent, or Firm* — Samuel R. McCoy, Jr.

(57) ABSTRACT

A new and distinct *Gonialoe variegata* cultivar named 'AMIAL1823' which is characterized by a short and compact plant size, thick succulent foliage covered with white subtuberculate spots arranged in irregular transverse rows and white, finely dentate leaf margins. The new variety has shown to be uniform and stable in the resulting generations from asexual propagation.

3 Drawing Sheets

Latin name of the genus and species: The Latin name of the genus and species of the novel variety disclosed herein is *Gonialoe variegata*.

Variety denomination: The inventive variety of *Gonialoe* disclosed herein has been given the variety denomination 'AMIAL1823'.

BACKGROUND OF THE INVENTION

Parentage: 'AMIAL1823' originated as a naturally occurring, whole-plant mutation of the species *Gonialoe* (not a named variety or cultivar). In the summer of 2013 the inventor discovered the mutation at a commercial greenhouse in Heerhugowaard, the Netherlands, growing amongst a crop of the species *Gonialoe variegata*. The mutation was noted for its compact size and strong foliage and was subsequently isolated for further evaluation in order to confirm the distinctness and stability of the characteristics first observed. Upon confirmation of distinctness and stability, 'AMIAL1823' was selected for commercialization in the autumn of 2013.

Asexual Reproduction: Asexual reproduction of the new cultivar 'AMIAL1823', by way of rooting leaf cuttings, was first initiated in the summer of 2014 at the inventor's commercial greenhouse in Heerhugowaard, the Netherlands. The claimed plant has since been asexually propagated by way of meristematic tissue culture propagation. Through six subsequent generations, the unique features of this cultivar have proven to be stable and true to type.

SUMMARY OF THE INVENTION

The cultivar 'AMIAL1823' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIAL1823'. These characteristics in combination distinguish 'AMIAL1823' as a new and distinct *Gonialoe variegate* cultivar:

1. 'AMIAL1823' exhibits a compact plant size with three-ranked foliage and a broad upright profile; and
2. 'AMIAL1823' exhibits strong, thick foliage; and
3. 'AMIAL1823' exhibits dark green foliage that is densely covered with prominent white subtuberculate spots on both the adaxial and abaxial surfaces which are arranged in irregular transverse rows; and
4. 'AMIAL1823' exhibits finely dentate foliage margins which are thinly margined white.

BOTANICAL DESCRIPTION OF THE PLANT

Figure 1:
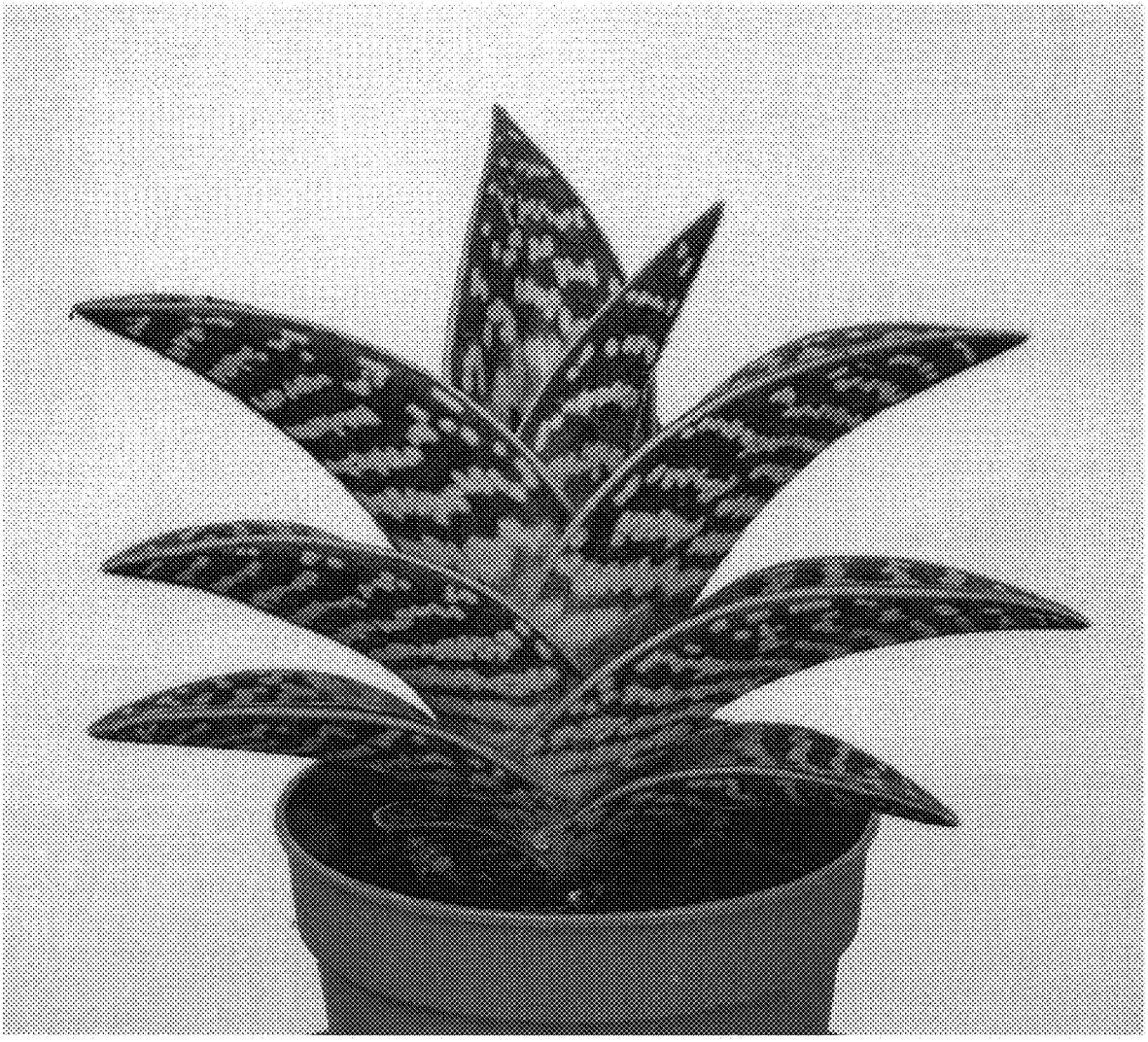
FIG. 1 illustrates, as nearly true as it is reasonably possible to make the same in color photographs of this type, an exemplary plant of 'AMIAL1823' grown in a commercial greenhouse in Heerhugowaard, the Netherlands. This plant is approximately 14 months old, shown planted in a 10 cm container.
Figure 2:
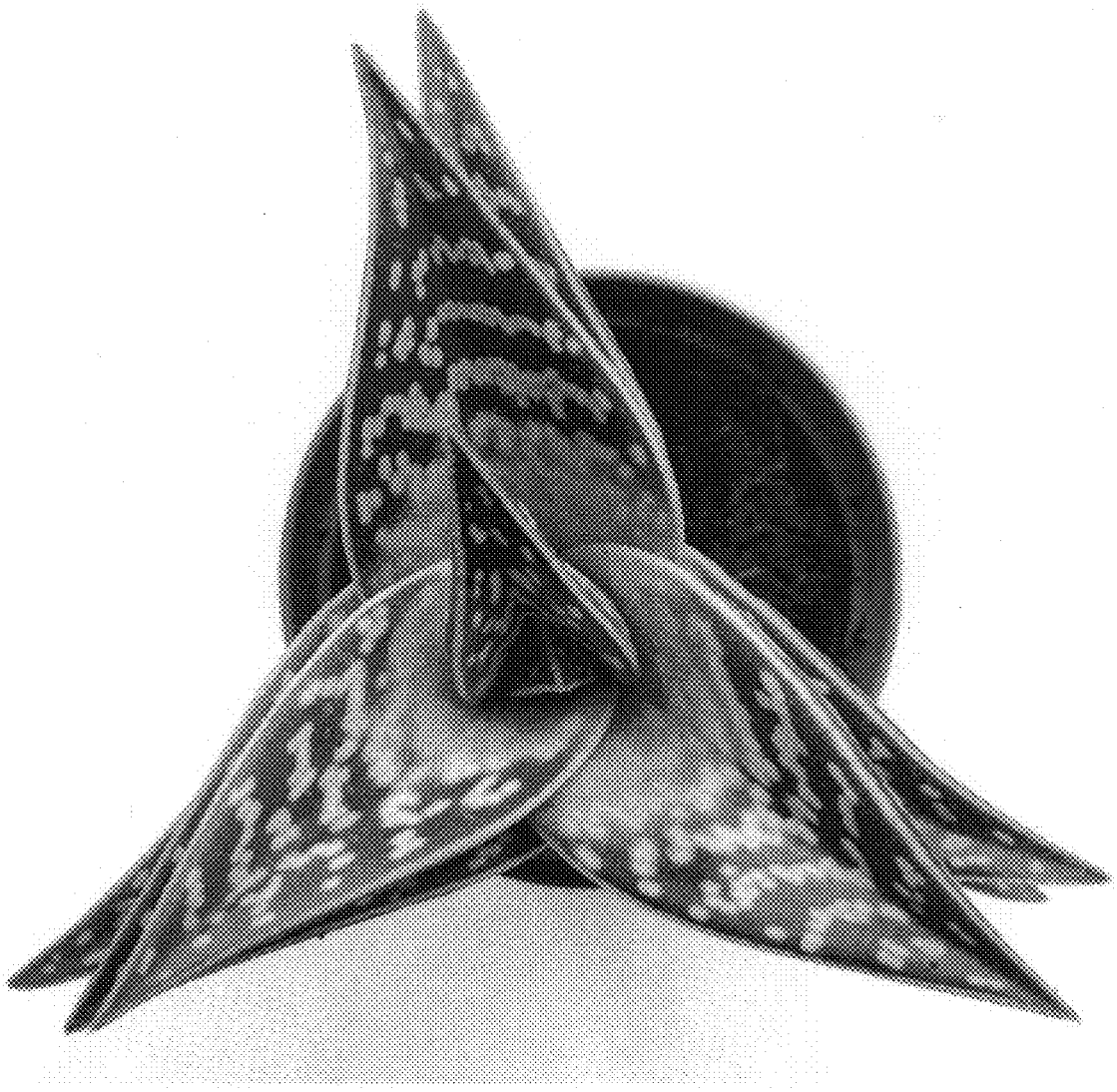
FIG. 2 illustrates, as nearly true as it is reasonably possible to make the same in color photographs of this type, the typical foliage arrangement of 'AMIAL1823'.
Figure 3:
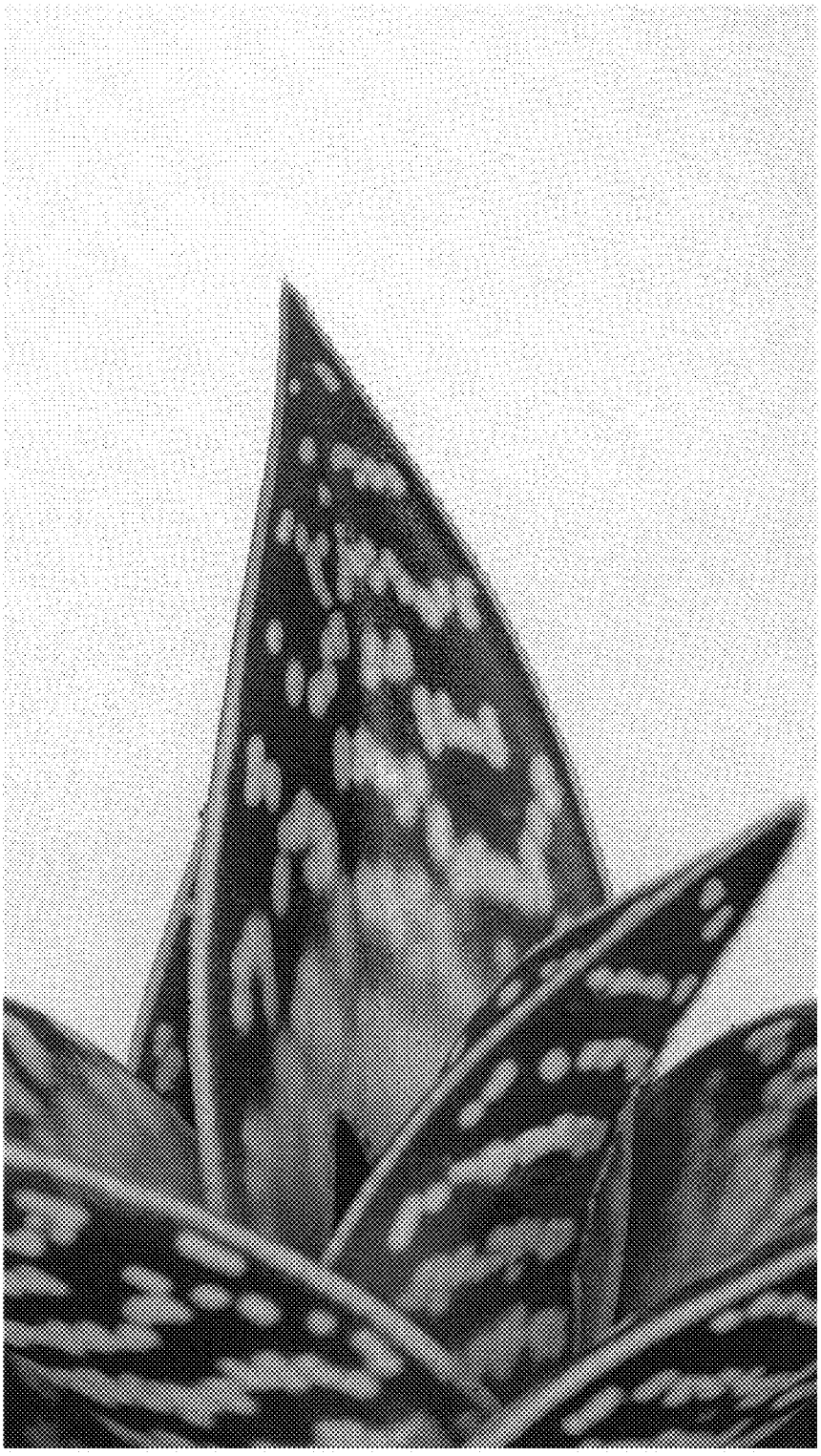
FIG. 3 illustrates, as nearly true as it is reasonably possible to make the same in color photographs of this type, the mature foliage 'AMIAL1823'.

The following observations and measurements made in August of 2018 describe averages from a sample set of six specimens of 14 months old 'AMIAL1823' plants grown in 12 cm nursery containers at commercial greenhouse in Heerhugowaard, the Netherlands. Plants were produced using conventional greenhouse production protocols for *Gonialoe* which consisted of minimal irrigation and fertilizer applications, and chemical pest and disease control measures against mealy bug, *Botrytis* and *Fusarium* as required. Plants were grown under approximately 50 percent shade and no photoperiodic treatments or artificial light was given to the plants.

Those skilled in the art will appreciate that certain characteristics will vary with older or, conversely, with younger plants. 'AMIAL1823' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIAL1823' and a comparison with the parent and closest known comparator, *Gonialoe variegata*, is provided below.

Plant description:

*Growth habit*.—Succulent perennial with three-ranked foliage.

*Plant shape*.—Broad upright.

*Height from soil level to top of foliar plane*.—16.4 cm.

*Plant spread*.—Average of 18.7 cm.

*Growth rate*.—Low to moderate.

*Plant vigor*.—Moderate.

*Propagation*.—Type — Leaf cuttings and meristematic tissue culture. Time to initiate rooting — Approximately 25 days at 18 degrees Celsius. Crop time — Approximately 52 weeks to produce a marketable plant in a 10 cm container.

*Disease and pest resistance or susceptibility*.—Neither resistance nor susceptibility to typical *Gonialoe variegata* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Three-ranked.

*Division*.—Simple.

*Attachment*.—Sessile.

*Quantity*.—Approximately 12 leaves.

*Shape*.—Thick, succulent leaves; ovate in shape.

*Dimensions*.—12.1 cm long, 5.2 cm wide, and 1.0 cm thick, on average.

*Aspect*.—Moderately carinate with the distal portion moderately curved downward.

*Attitude*.—Upward and outward at an approximate angle of 45 degrees to horizontal.

*Apex*.—Apiculate with a soft mucronulate tip.

*Base*.—Broad cuneate.

*Margin*.—Finely dentate; teeth have an average length of 0.5 mm and are colored greyed-green, nearest to RHS 192D. Margins are not undulated or lobed.

*Texture, adaxial surface*.—Glabrous and densely covered with elliptical to oblong subtuberculate spots arranged in irregular transverse rows across the leaf surface.

*Texture, abaxial surface*.—Glabrous and densely covered with elliptical to oblong subtuberculate spots arranged in irregular transverse rows across the leaf surface. The midrib is finely dentate; teeth are approximately 0.5 mm long and are colored greyed-green, nearest to RHS 192D.

*Luster, adaxial surface*.—Very slightly glossy.

*Luster, abaxial surface*.—Matte.

*Color*.—Juvenile foliage, adaxial surface — Green, nearest to RHS NN137A, and fading to yellow-green towards the base, nearest to a combination of RHS 144A and 144B. Juvenile foliage, abaxial surface — Nearest to in between green and yellow-green, RHS NN137A and 147A, and fading to yellow-green towards the base, nearest to a combination of RHS 144A and 144B. Mature foliage, adaxial surface — Nearest to in between green and yellow-green, RHS NN137B and 147A; suffused with greyed-green towards the base, nearest to RHS 191C. Mature foliage, abaxial surface — Nearest to in between green and yellow-green, RHS 139A and 147A; fading to a mixture of green and yellow-green towards the base, nearest to RHS 143C and 144A.

*Venation*.—No venation is visible.

*Subtuberculate spots, adaxial surface*.—Shape — Elliptic. Dimensions — 5.0 mm long and 2.0 mm wide. Texture — Smooth and glabrous. Color, juvenile foliage — Greyed-green, nearest to RHS 192C. Color, mature foliage — Greyed-green, nearest to in between RHS 191C and 191D.

*Subtuberculate spots, abaxial surface*.—Shape — Elliptic. Dimensions — 5.0 mm long and 2.0 mm wide. Texture — Smooth and glabrous. Color, juvenile foliage — Greyed-green, nearest to RHS 192C. Color, mature foliage — Greyed-green, nearest to RHS 192C.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIAL1823' differ from the parent, *Gonialoe variegata*, in the following characteristics described in Table 1 below.

TABLE 1

| Characteristic | 'AMIAL1823' | Gonialoe variegata |
|---|---|---|
| Plant height. | Shorter than the parent. | Taller than AMIAL1823'. |
| Leaf apex. | Acute. | Apiculate with a soft mucronulate tip. |
| Leaf strength. | Stronger than the parent. | Weaker than 'AMIAL1823'. |

COMPARISONS WITH THE CLOSEST KNOWN COMPARATOR

Plants of the new cultivar 'AMIAL1823' differ from the commercial variety, *Aloe aristata* x *Haworthia limifolia* 'AMIAL1601' (U.S. patent application Ser. No. 15/932,615) in the following characteristics described in Table 2 below.

TABLE 2

| Characteristic | 'AMIAL1823' | 'AMIAL1601' |
|---|---|---|
| Foliage thickness. | Thicker than 'AMIAL1601'. | Thinner than 'AMIAL1823'. |
| Foliage subtuber culate spots. | Larger than those of 'AMIAL1601' and shaped elliptical to oblong. | Smaller than those of 'AMIAL1823' and orbicular-shaped. |
| Foliage margins. | Finely dentate with smaller teeth than those of 'AMIAL1601'. | Finely dentate with larger teeth than those of 'AMIAL1823'. |
| General coloration of the mature foliage. | Darker shade of green. | Lighter shade of green. |

That which is claimed is:

1. A new and distinct variety of *Gonialoe variegata* plant named 'AMIAL1823', substantially as described and illustrated herein.

* * * * *